US012033732B2

(12) United States Patent
Speirs

(10) Patent No.: US 12,033,732 B2
(45) Date of Patent: Jul. 9, 2024

(54) RISK-VALUE HEALTHCARE DELIVERY SYSTEM AND METHOD

(71) Applicant: Shane Ryan Speirs, Phoenix, AZ (US)

(72) Inventor: Shane Ryan Speirs, Phoenix, AZ (US)

(73) Assignee: ADAGEIS, LLC, Scottsdale, AZ (US)

( * ) Notice: Subject to any disclaimer, the term of this patent is extended or adjusted under 35 U.S.C. 154(b) by 0 days.

(21) Appl. No.: 17/464,283

(22) Filed: Sep. 1, 2021

(65) Prior Publication Data
US 2022/0115098 A1    Apr. 14, 2022

Related U.S. Application Data

(60) Provisional application No. 63/089,169, filed on Oct. 8, 2020.

(51) Int. Cl.
*G16H 10/60*    (2018.01)
*G16H 50/30*    (2018.01)

(52) U.S. Cl.
CPC ............. *G16H 10/60* (2018.01); *G16H 50/30* (2018.01)

(58) Field of Classification Search
CPC ................................ G16H 10/60; G16H 50/30
See application file for complete search history.

(56) References Cited

U.S. PATENT DOCUMENTS

| | | | | |
|---|---|---|---|---|
| 2004/0138925 A1* | 7/2004 | Zheng | .................... | G06Q 10/10 |
| | | | | 705/2 |
| 2006/0287890 A1* | 12/2006 | Stead | ..................... | G16H 10/20 |
| | | | | 705/3 |
| 2010/0131434 A1* | 5/2010 | Magent | .................. | G16H 10/60 |
| | | | | 706/14 |
| 2013/0030260 A1* | 1/2013 | Hale | ....................... | G16H 50/30 |
| | | | | 600/301 |
| 2014/0037739 A1* | 2/2014 | Schentag | ............... | G01N 33/66 |
| | | | | 514/23 |
| 2014/0108042 A1 | 4/2014 | Reddy et al. | | |

(Continued)

FOREIGN PATENT DOCUMENTS

WO    2022076113    4/2022

OTHER PUBLICATIONS

Written Opinion of the International Search Authority issued in PCT/US21/48716 on Dec. 14, 2021.

(Continued)

*Primary Examiner* — Fonya M Long
*Assistant Examiner* — Anthony Balaj
(74) *Attorney, Agent, or Firm* — SNELL & WILMER L.L.P.

(57) ABSTRACT

The system determines reimbursements to healthcare providers that provide care based on a novel risk-value reimbursement model, wherein the care is based on a patient risk score and the quality of care delivered. The system and method may include the process of obtaining variables of patient health data for a patient; determining a rank order correlation of the variables with an adverse health outcome; determining a risk score for the patient; sorting patient panels based on the risk score for each patient in the patient panel; determining a lower amount of time on a timer for a chart for the patient, in response to the risk score for the patient being higher than other risk scores for other patients in the patient panel; and resetting the timer, in response to an action by a provider.

20 Claims, 1 Drawing Sheet

(56) References Cited

U.S. PATENT DOCUMENTS

| | | | | |
|---|---|---|---|---|
| 2014/0108044 A1* | 4/2014 | Reddy | ............... | G06Q 10/10 |
| | | | | 705/3 |
| 2014/0164006 A1 | 6/2014 | Merkin | | |
| 2014/0324451 A1 | 10/2014 | Pesot et al. | | |
| 2015/0066521 A1* | 3/2015 | Buckley | ............... | G16Z 99/00 |
| | | | | 705/2 |
| 2015/0254956 A1* | 9/2015 | Shen | ............... | A61B 5/445 |
| | | | | 340/573.1 |
| 2016/0125168 A1* | 5/2016 | Aagesen | ............... | G16H 10/60 |
| | | | | 705/3 |
| 2017/0323081 A1* | 11/2017 | Govro | ............... | G16H 10/60 |
| 2018/0260925 A1* | 9/2018 | Gotz | ............... | G16H 50/70 |
| 2019/0051389 A1* | 2/2019 | Meittunen | ............... | G16H 40/20 |
| 2020/0242566 A1* | 7/2020 | Agarwal | ............... | G06N 7/01 |
| 2020/0256878 A1* | 8/2020 | Dart | ............... | G16H 70/60 |
| 2021/0193324 A1* | 6/2021 | Truschel | ............... | G16H 10/60 |
| 2022/0051787 A1* | 2/2022 | Sugai | ............... | A61B 5/746 |
| 2022/0341951 A1* | 10/2022 | Beckley | ............... | G01N 33/5308 |

OTHER PUBLICATIONS

The International Bureau of WIPO, International Preliminary Report on Patentability dated Apr. 20, 2023 in Application No. PCT/US2021/48716.

* cited by examiner

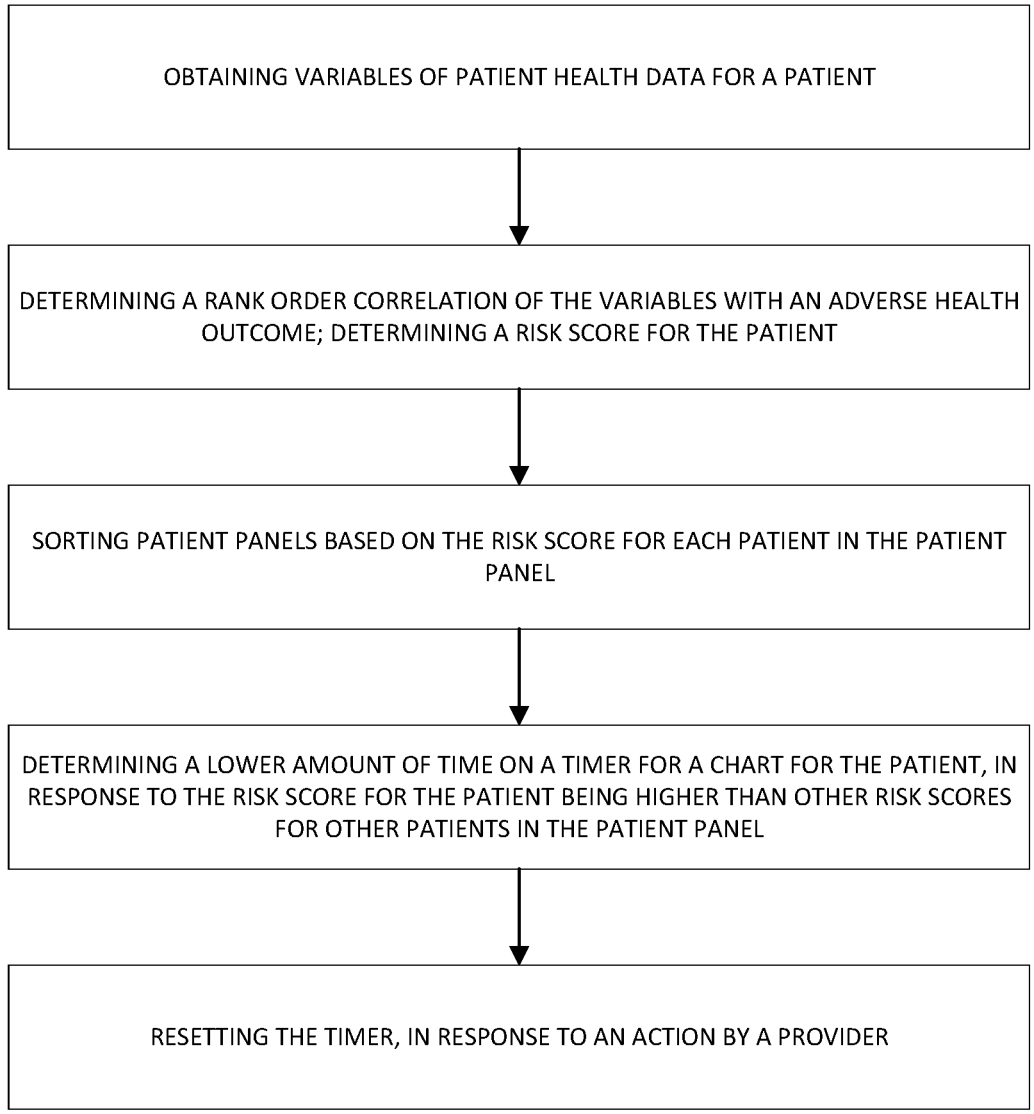

RISK-VALUE HEALTHCARE DELIVERY SYSTEM AND METHOD

CROSS-REFERENCE TO RELATED APPLICATIONS

This application claims priority to and the benefit of U.S. Provisional Patent Application No. 63/089,169 entitled Risk-Value Healthcare Delivery System and Method filed Oct. 8, 2020, the entire contents of which is incorporated by reference herein for all purposes.

TECHNICAL FIELD

The present disclosure generally relates to a healthcare delivery system, and more particularly, to a system that determines care based on a patient risk score and the quality of care.

BACKGROUND

Healthcare organizations often get paid for the services they provide to patients based on healthcare reimbursement models. A healthcare organization may adopt one of many types of reimbursement models available in the United States, depending on the goals and functions of the healthcare organization and its relationships with its patients.

Care delivery models are typically based on how the medical provider is reimbursed. The different models that are more common for healthcare reimbursement include fee-for-service, value-based care, bundled payments, accountable care, patient-centered medical home, pathways model, health maintenance organizations, and preferred provider organizations. A patient must interact with a medical provider in order to create a billable visit. Historically, more complex patient visits result in higher billable services.

A fee-for-service model is typically a model by which patient pricing is based on the cost of each individual service or product that a medical provider orders. As a result, a provider receives a higher payment when the provider provides more services to its patients. However, such a system can lead to redundancy (ordering of unnecessary testing and procedures) or service inflation.

A value-based care model (or pay-for-performance model) is typically a billing system that is becoming more common in healthcare, and governments often favor this model. This value-based model reimburses providers based on the quality of care they provide to their patients, rather than the quantity. This value-based model often eliminates (or reduces) overcharging and service inflation from fee-for-service models. This value-based model incentivizes providers to meet performance metrics. This value-based model places the responsibility of quality service on the healthcare providers.

Bundled payments are a subtype of value-based care, where a patient has a set bill for a single "episode" of care. The billings then get split among the providers involved in the care. With bundled payments, providers must assume some risk and it encourages the use of efficient ways to treat patients.

Another form of value-based care is an Accountable Care Organization (ACO). An ACO typically includes a group of healthcare providers of varying specialties that come together to provide comprehensive care services any requesting patients. ACOs usually work together to provide checks, balances, and accountability to ensure minimal overlap and minimized cost.

A Patient-Centered Medical Home is similar to an ACO, but instead of existing as a provider reimbursement method, a patient-centered medical home provides holistic and personalized care.

A Health Maintenance Organization (HMO) is typically a model of care in which a patient works with an organization for both healthcare insurance and healthcare delivery.

SUMMARY

In various embodiments, the system and method may include the process of obtaining, by a computer, variables of patient health data for a patient; determining, by the computer, a rank order correlation of the variables with an adverse health outcome; determining, by the computer, a risk score for the patient; sorting, by the computer, patient panels based on the risk score for each patient in the patient panel; determining, by the computer, a lower amount of time on a timer for a chart for the patient, in response to the risk score for the patient being higher than other risk scores for other patients in the patient panel; and resetting, by the computer, the timer, in response to an action by a provider.

The variables may include at least one of patient diagnoses, vital signs or lab values. The adverse health outcome may comprise hospitalization within a time period (e.g. a past year), a fall sustained by a patient within a set period of time, or the death of a patient. The system may associate the timer with the chart for each patient in the patient panel. The provider action may include at least one of opening the chart, viewing a lab value, documenting a finding or documenting an encounter with the patient. The provider action may depend on at least one of the medical provider or organizational preference. The system may further comprise queuing the chart higher in a queue, in response to the risk score for the patient being higher than other risk scores for other patients in the patient panel. The system may further comprise notifying the provider in response to the timer being at a predetermined time.

The risk score may be based on (Patient Diagnosis Codes*Patient Diagnosis Codes Correlation with adverse health outcome)+(Patient Lab Values*Patient Lab Values Correlation with adverse health outcome)+(Patient Vitals*Patient Vitals Correlation with adverse health outcome).

BRIEF DESCRIPTION OF THE DRAWINGS

The subject matter of the present disclosure is particularly pointed out and distinctly claimed in the concluding portion of the specification. A more complete understanding of the present disclosure, however, may best be obtained by referring to the detailed description and claims when considered in connection with the drawing FIGURES.

FIG. 1 shows an exemplary flow chart, in accordance with various embodiments.

DETAILED DESCRIPTION

In general, the system determines reimbursements to healthcare providers that provide care based on a novel risk-value reimbursement model, wherein the care is based on a patient risk score and the quality of care delivered.

In various embodiments, the system computes a patient risk-score by using a patient's health information. The health information may include a medical diagnosis charted with corresponding diagnosis codes (e.g., from the International Classification of Diseases (ICD)), patient vitals (e.g., oxygen saturation and blood pressure), patient lab values (e.g., hemoglobin A1c, hematocrit), and/or other patient qualities (e.g., patient age or patient weight). The patient risk scores of individualized patients may be added to generate a provider patient panel risk-score. The medical provider may be reimbursed based in part on this provider patient panel risk-score of the entire patient panel.

In various embodiments, the system may also determine reimbursement to providers based on the quality of care the providers provide to their patients. The quality of care may be measured by various quality metrics. The quality metrics may be set by an organization using the model of care. For example, a quality metric may be the provider providing smoking cessation counseling. The higher percentage of the provider's patient panel that are smokers that receive smoking cessation counseling, the higher the medical provider is reimbursed. Therefore, the reimbursement model is considered a risk score-value based care model, or otherwise known as a risk-value care model.

The system may sort a panel of patients by risk-score, or a patient's risk of an adverse health outcome. By doing this, the software is allocating more resources to the population's higher risk (risk score) patients, while also encouraging providers to improve the health of their patients by reimbursing at a higher level for higher quality care. By using this system, a provider may have 1000 higher risk patients, and be reimbursed the same as a provider that has 2000 lower risk patients.

More particularly, in various embodiments, the system may use patient data modeling that uses a value structure that is based in utility theory. The structure is that patient "attributes" define and describe the value of the thing of interest. These are combined into a "value function", or a value-based algorithm. The model may include multiple attributes, so it is a "multi-attribute value (or utility) function" that defines and quantifies the "value" of the thing being evaluated. The patient "attributes" may be patient health information. The "multi-attribute value" may be computed using the value-based algorithm to obtain patient risk (the thing of interest), or risk-score.

The system models health data for a panel of patients, and analyzes each health data variable with the presence or absence of an adverse health event. The system uses the health data for a panel of patients and a number of health data variables are analyzed. The system computes rank order correlation, or the statistical dependence between the rankings of two variables. For example, a particular health data variable common to a subset of patients within the panel and an adverse health event. This assesses how well the relationship between the two variables can be described. The correlation between two variables will be high when observations have a similar rank between the two variables, and the correlation between two variables are low when observations have a dissimilar rank between the two variables.

By modeling data in this way, the system calculates the risk of each patient by using a correlation model for the panel of patients. The correlation model correlates patient health data (e.g., medical diagnoses, diagnosis codes associated with medical diagnoses, lab values, vitals, and other aspects of a patient's medical information) with adverse outcomes (e.g., hospitalizations, falls or death). The correlation includes computing information from a patient panel, as described above. The model then uses the correlation coefficients for each health data variable based on its relation to the adverse health outcome, in a value-based algorithm to assess individual patient risk.

In various embodiments, a correlation may be computed for each patient diagnosis code. For example, for a patient having a diagnosis of COPD exacerbation, a medical provider would assign the ICD code J44.1: Chronic Obstructive Pulmonary disease with acute exacerbation to the patient chart. Such a diagnosis may have a higher correlation with hospitalizations in the last year than a patient having a diagnosis of Ankle Sprain, wherein a medical provider would assign the ICD code S93.401 Sprain of unspecified ligament of ankle.

In a similar manner, a correlation is computed for Hemoglobin A1c. For example, a patient with a Hemoglobin A1c of 14.2 (a lab value a patient may have in their chart) may have a higher correlation with hospitalizations in the last year than a patient having a Hemoglobin Mc of 6.6.

In various embodiments, a value-based algorithm for risk score may be calculated in the following way:

> Patient Risk Score=(Patient Diagnosis Codes*Patient Diagnosis Codes Correlation with adverse health outcome)+(Patient Lab Values*Patient Lab Values Correlation with adverse health outcome)+(Patient Vitals*Patient Vitals Correlation with adverse health outcome)

(+) denotes addition (*) denotes multiplication

An example of this risk score algorithm with a subset of a patient's health data is given below. Note that this example only includes part of a patient's health data. In various embodiments, the algorithm may use a larger subset of a patient's health data or all available health data from that patient.

> Patient Risk score=(Diabetes Mellitus with hyperglycemia (E11.65)*Diabetes Mellitus with hyperglycemia correlation with hospitalization in last 1 year)+(Hemoglobin A1c analog value*Hemoglobin A1c correlation with hospitalization in last 1 year)+(Patient weight analog value*Patient weight correlation with hospitalization in last 1 year)

The system may obtain the patient data by using an application programming interface (API) which interfaces with existing electronic medical records (EMR) or electronic health records (EHR) software, or the patient data may be obtained from a stand-alone EMR/EHR software platform that has the functionality embedded in the technology.

In various embodiments, steps for an API software may include the following:

Patient health data is obtained from an Electronic Medical Record system and/or a patient database or app (e.g. Fitbit). The patient health data may include patient diagnoses, vital signs, lab values, etc. which are known as variables.

A rank order correlation of the variables is computed with an adverse health outcome such as at least one of hospitalization within a time period, a fall sustained by a patient within a time period, or the death of a patient.

The risk score for an individual patient is computed. The computation may use a value based algorithm, by multiplying each variable with its corresponding rank order correlation to an adverse health outcome, then summing the values of each variable and rank order correlation together to create a risk score. The variables for the algorithm may be chosen as a subset of variables from the patient's health data, or the all variables from the patient's health data.

The system sorts the patient panels by patient risk score. A patient panel may be a subset of patients in a population for which a medical provider oversees care for.

The system may assign a timer for each patient, or patient chart. When the timer is up, the medical provider may be expected to view that patient chart within a standard amount of time, as set by the user or organization. As such, the timer function may, when the timer reaches a predetermined time or runs out of time, notify the medical provider to review the appropriate chart by sending the medical provider a text, flashing the screen, displaying the appropriate chart, notifying the medical provider's assistant, etc. The timer function may be correlated with the patient risk score, so the timer will be shorter (faster to run out of time) if the patient's risk score is higher.

In response to an action associated with the patient's medical chart by the medical provider, the timer may be reset. The action associated with the patient's medical chart may include the medical provider opening the medical chart, viewing a lab value, writing a note documenting a finding, or documenting an encounter with a patient. The resetting of the timer results in a medical provider being queued more frequently to enter the patient chart, in response to a higher patient's risk score (the higher the risk of the patient having an adverse health outcome).

In various embodiments, the system may include an interface that allows the provider to view the entire patient panel based on risk score. By doing this, the system identifies the patients that have a high likelihood of an adverse health outcome (the higher the risk score, the higher the likelihood of an adverse health outcome). By providing the timer, sorting the patient panel and providing notifications, the system then encourages (or makes suggestions to) the medical provider to allocate more of their time and resources to higher risk score patients, or to oversee the high risk patient's charts more frequently.

The system uses this risk score so that higher risk patients are more frequently at the top of the list, with the timer set to have the higher risk patients be viewed more often than low risk patients. This is accomplished by the timer functionality based on risk. The timer function correlates with patient risk score, so the timer will be shorter (faster to run out of time) if the patient's risk score is higher. For example, a very high risk patient may appear at the top of the medical provider's patient panel list sooner than a low risk patient, if the medical provider were to view the high risk patient chart and the low risk patient chart at the same time. This timer mechanism may be reset whenever the provider enters the patient's chart. The resetting may be based on simply opening the patient chart, viewing a lab value, writing a note, documenting a finding, or documenting an encounter with a patient. Such actions may be monitored by the timer function or such actions may send a signal to the timer function, causing the timer function to reset. The factors for resetting the time may depend on medical provider, hospital and/or organizational preference.

Within this API or EMR/EHR, the provider is also able to view appointments by day, as well as their task inbox. Using this system, providers are expected to enter patient charts before the timer runs out, within a specified amount of time to be set by the individual user or organization. This leads to the patient being cared for outside of office visits, and offers frequent viewing of patient medical information, leading to improvement in care management, and therefore, the health of individual patients and the patient panel (population) as a whole.

The system may provide reporting functions to medical providers and/or administrators, wherein the report may include a list of times, the average time or any other statistics about the time a medical provider took to start reviewing a chart, how much time was left on the timer when the provider started reviewing the chart, how many times the system needed to send a notification to the provider, how many times a chart was reviewed during a time period or similar data related to the timer function. The system may automatically set an appointment for the patient to connect with the provider, based on the provider's review of the chart a predetermined number of times and/or based on the provider's actions with the chart. In that regard, the system may be integrated with the provider scheduling system and/or the patient's calendar to determine open time slots for the provider and patient to connect.

Based on provider input, the system may communicate with the patient's apps or devices. For example, the system may send a notification to a patient's shopping list to suggest buying new or different types of food. The system may send a notification to a patient's workout app or Fitbit to increase or decrease certain exercises, or to restrict workouts that may cause the patient to increase heart rate or blood oxygen above a certain level.

The detailed description of various embodiments herein makes reference to the accompanying drawings and pictures, which show various embodiments by way of illustration. While these various embodiments are described in sufficient detail to enable those skilled in the art to practice the disclosure, it should be understood that other embodiments may be realized and that logical and mechanical changes may be made without departing from the spirit and scope of the disclosure. Thus, the detailed description herein is presented for purposes of illustration only and not for purposes of limitation. For example, the steps recited in any of the method or process descriptions may be executed in any order and are not limited to the order presented. Moreover, any of the functions or steps may be outsourced to or performed by one or more third parties. Modifications, additions, or omissions may be made to the systems, apparatuses, and methods described herein without departing from the scope of the disclosure. For example, the components of the systems and apparatuses may be integrated or separated. Moreover, the operations of the systems and apparatuses disclosed herein may be performed by more, fewer, or other components and the methods described may include more, fewer, or other steps. Additionally, steps may be performed in any suitable order. As used in this document, "each" refers to each member of a set or each member of a subset of a set. Furthermore, any reference to singular includes plural embodiments, and any reference to more than one component may include a singular embodiment Although specific advantages have been enumerated herein, various embodiments may include some, none, or all of the enumerated advantages.

Systems, methods, and computer program products are provided. In the detailed description herein, references to "various embodiments," "one embodiment," "an embodiment," "an example embodiment," etc., indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to affect such feature, structure, or characteristic in connection with other embodiments whether or not explicitly described. After reading the description, it will be apparent to one skilled in the relevant art(s) how to implement the disclosure in alternative embodiments.

Terms and phrases similar to "associate" and/or "associating" may include tagging, flagging, correlating, using a look-up table or any other method or system for indicating or creating a relationship between elements, such as, for example, (i) a transaction account and (ii) an item (e.g., offer, reward, discount) and/or digital channel. Moreover, the associating may occur at any point, in response to any suitable action, event, or period of time. The associating may occur at pre-determined intervals, periodically, randomly, once, more than once, or in response to a suitable request or action. Any of the information may be distributed and/or accessed via a software enabled link, wherein the link may be sent via an email, text, post, social network input, and/or any other method known in the art.

Benefits, other advantages, and solutions to problems have been described herein with regard to specific embodiments. However, the benefits, advantages, solutions to problems, and any elements that may cause any benefit, advantage, or solution to occur or become more pronounced are not to be construed as critical, required, or essential features or elements of the disclosure. The scope of the disclosure is accordingly limited by nothing other than the appended claims, in which reference to an element in the singular is not intended to mean "one and only one" unless explicitly so stated, but rather "one or more." Moreover, where a phrase similar to 'at least one of A, B, and C' or 'at least one of A, B, or C' is used in the claims or specification, it is intended that the phrase be interpreted to mean that A alone may be present in an embodiment, B alone may be present in an embodiment, C alone may be present in an embodiment, or that any combination of the elements A, B and C may be present in a single embodiment; for example, A and B, A and C, B and C, or A and B and C. Although the disclosure includes a method, it is contemplated that it may be embodied as computer program instructions on a tangible computer-readable carrier, such as a magnetic or optical memory or a magnetic or optical disk. All structural, chemical, and functional equivalents to the elements of the above-described various embodiments that are known to those of ordinary skill in the art are expressly incorporated herein by reference and are intended to be encompassed by the present claims. Moreover, it is not necessary for a device or method to address each and every problem sought to be solved by the present disclosure for it to be encompassed by the present claims. Furthermore, no element, component, or method step in the present disclosure is intended to be dedicated to the public regardless of whether the element, component, or method step is explicitly recited in the claims. No claim element is intended to invoke 35 U.S.C. § 112(f) unless the element is expressly recited using the phrase "means for" or "step for". As used herein, the terms "comprises," "comprising," or any other variation thereof, are intended to cover a non-exclusive inclusion, such that a process, method, article, or apparatus that comprises a list of elements does not include only those elements but may include other elements not expressly listed or inherent to such process, method, article, or apparatus.

Any of the users may interact with the system or the charts via any user interface known in the art or hereinafter developed. In various embodiments, the system and various components may integrate with one or more smart digital assistant technologies. For example, exemplary smart digital assistant technologies may include the ALEXA® system developed by the AMAZON® company, the GOOGLE HOME® system developed by Alphabet, Inc., the HOMEPOD® system of the APPLE® company, and/or similar digital assistant technologies. The ALEXA® system, GOOGLE HOME® system, and HOMEPOD® system, may each provide cloud-based voice activation services that can assist with tasks, entertainment, general information, and more. All the ALEXA® devices, such as the AMAZON ECHO®, AMAZON ECHO DOT®, AMAZON TAP®, and AMAZON FIRE® TV, have access to the ALEXA® system. The ALEXA® system, GOOGLE HOME® system, and HOMEPOD® system may receive voice commands via its voice activation technology, activate other functions, control smart devices, and/or gather information. For example, the smart digital assistant technologies may be used to interact with music, emails, texts, phone calls, question answering, home improvement information, smart home communication/activation, games, shopping, making to-do lists, setting alarms, streaming podcasts, playing audiobooks, and providing weather, traffic, and other real time information, such as news. The ALEXA®, GOOGLE HOME®, and HOMEPOD® systems may also allow the user to access information about eligible patient accounts, hospital accounts, vendor accounts or transaction accounts linked to an online account across all digital assistant-enabled devices.

The various machines and tools may include internet of things (IOT) technology such that the machines and tools may automatically provide status updates and data to the system. The system may also automatically notify the medical providers. The present system or any part(s) or function(s) thereof may be implemented using hardware, software, or a combination thereof and may be implemented in one or more computer systems or other processing systems. However, the manipulations performed by embodiments may be referred to in terms, such as matching or selecting, which are commonly associated with mental operations performed by a human operator. No such capability of a human operator is necessary, or desirable, in most cases, in any of the operations described herein. Rather, the operations may be machine operations or any of the operations may be conducted or enhanced by artificial intelligence (AI) or machine learning. AI may refer generally to the study of agents (e.g., machines, computer-based systems, etc.) that perceive the world around them, form plans, and make decisions to achieve their goals. Foundations of AI include mathematics, logic, philosophy, probability, linguistics, neuroscience, and decision theory. Many fields fall under the umbrella of AI, such as computer vision, robotics, machine learning, and natural language processing. Useful machines for performing the various embodiments include general purpose digital computers or similar devices.

Computer programs (also referred to as computer control logic) are stored in main memory and/or secondary memory. Computer programs may also be received via communications interface. Such computer programs, when executed, enable the computer system to perform the features as discussed herein. In particular, the computer programs, when executed, enable the processor to perform the features of various embodiments. Accordingly, such computer programs represent controllers of the computer system.

These computer program instructions may be loaded onto a general purpose computer, special purpose computer, or other programmable data processing apparatus to produce a machine, such that the instructions that execute on the computer or other programmable data processing apparatus create means for implementing the functions specified in the flowchart block or blocks. These computer program instructions may also be stored in a computer-readable memory that can direct a computer or other programmable data processing apparatus to function in a particular manner, such that the instructions stored in the computer-readable memory produce an article of manufacture including instruction means which implement the function specified in the flowchart block or blocks. The computer program instructions may also be loaded onto a computer or other programmable data processing apparatus to cause a series of operational steps to be performed on the computer or other programmable apparatus to produce a computer-implemented process such that the instructions which execute on the computer or other programmable apparatus provide steps for implementing the functions specified in the flowchart block or blocks.

In various embodiments, software may be stored in a computer program product and loaded into a computer system using a removable storage drive, hard disk drive, or communications interface. The control logic (software), when executed by the processor, causes the processor to perform the functions of various embodiments as described herein. In various embodiments, hardware components may take the form of application specific integrated circuits (ASICs). Implementation of the hardware so as to perform the functions described herein will be apparent to persons skilled in the relevant art(s).

As will be appreciated by one of ordinary skill in the art, the system may be embodied as a customization of an existing system, an add-on product, a processing apparatus executing upgraded software, a stand-alone system, a distributed system, a method, a data processing system, a device for data processing, and/or a computer program product. Accordingly, any portion of the system or a module may take the form of a processing apparatus executing code, an internet based embodiment, an entirely hardware embodiment, or an embodiment combining aspects of the internet, software, and hardware. Furthermore, the system may take the form of a computer program product on a computer-readable storage medium having computer-readable program code means embodied in the storage medium. Any suitable computer-readable storage medium may be utilized, including hard disks, CD-ROM, BLU-RAY DISC®, optical storage devices, magnetic storage devices, and/or the like.

In various embodiments, components, modules, and/or engines of the system may be implemented as micro-applications or micro-apps. Micro-apps are typically deployed in the context of a mobile operating system, including for example, a WINDOWS® mobile operating system, an ANDROID® operating system, an APPLE® iOS operating system, a BLACKBERRY® company's operating system, and the like. The micro-app may be configured to leverage the resources of the larger operating system and associated hardware via a set of predetermined rules which govern the operations of various operating systems and hardware resources. For example, where a micro-app desires to communicate with a device or network other than the mobile device or mobile operating system, the micro-app may leverage the communication protocol of the operating system and associated device hardware under the predetermined rules of the mobile operating system. Moreover, where the micro-app desires an input from a user, the micro-app may be configured to request a response from the operating system which monitors various hardware components and then communicates a detected input from the hardware to the micro-app.

The system and method may be described herein in terms of functional block components, screen shots, optional selections, and various processing steps. It should be appreciated that such functional blocks may be realized by any number of hardware and/or software components configured to perform the specified functions. For example, the system may employ various integrated circuit components, e.g., memory elements, processing elements, logic elements, look-up tables, and the like, which may carry out a variety of functions under the control of one or more microprocessors or other control devices. Similarly, the software elements of the system may be implemented with any programming or scripting language such as C, C++, C#, JAVA®, JAVASCRIPT®, JAVASCRIPT® Object Notation (JSON), VBScript, Macromedia COLD FUSION, COBOL, MICROSOFT® company's Active Server Pages, assembly, PERL®, PHP, awk, PYTHON®, Visual Basic, SQL Stored Procedures, PL/SQL, any UNIX® shell script, and extensible markup language (XML) with the various algorithms being implemented with any combination of data structures, objects, processes, routines or other programming elements. Further, it should be noted that the system may employ any number of conventional techniques for data transmission, signaling, data processing, network control, and the like. Still further, the system could be used to detect or prevent security issues with a client-side scripting language, such as JAVASCRIPT®, VBScript, or the like.

The system and method are described herein with reference to screen shots, block diagrams and flowchart illustrations of methods, apparatus, and computer program products according to various embodiments. It will be understood that each functional block of the block diagrams and the flowchart illustrations, and combinations of functional blocks in the block diagrams and flowchart illustrations, respectively, can be implemented by computer program instructions.

Accordingly, functional blocks of the block diagrams and flowchart illustrations support combinations of means for performing the specified functions, combinations of steps for performing the specified functions, and program instruction means for performing the specified functions. It will also be understood that each functional block of the block diagrams and flowchart illustrations, and combinations of functional blocks in the block diagrams and flowchart illustrations, can be implemented by either special purpose hardware-based computer systems which perform the specified functions or steps, or suitable combinations of special purpose hardware and computer instructions. Further, illustrations of the process flows and the descriptions thereof may make reference to user WINDOWS® applications, webpages, websites, web forms, prompts, etc. Practitioners will appreciate that the illustrated steps described herein may comprise, in any number of configurations, including the use of WINDOWS® applications, webpages, web forms, popup WINDOWS® applications, prompts, and the like. It should be further appreciated that the multiple steps as illustrated and described may be combined into single webpages and/or WINDOWS® applications but have been expanded for the sake of simplicity. In other cases, steps illustrated and described as single process steps may be separated into multiple webpages and/or WINDOWS® applications but have been combined for simplicity.

In various embodiments, the software elements of the system may also be implemented using a JAVASCRIPT® run-time environment configured to execute JAVASCRIPT® code outside of a web browser. For example, the software elements of the system may also be implemented using NODE.JS® components. NODE.JS® programs may implement several modules to handle various core functionalities. For example, a package management module, such as NPM®, may be implemented as an open source library to aid in organizing the installation and management of third-party NODE.JS® programs. NODE.JS® programs may also implement a process manager, such as, for example, Parallel Multithreaded Machine ("PM2"); a resource and performance monitoring tool, such as, for example, Node Application Metrics ("appmetrics"); a library module for building user interfaces, and/or any other suitable and/or desired module.

Middleware may include any hardware and/or software suitably configured to facilitate communications and/or process transactions between disparate computing systems. Middleware components are commercially available and known in the art. Middleware may be implemented through commercially available hardware and/or software, through custom hardware and/or software components, or through a combination thereof. Middleware may reside in a variety of configurations and may exist as a standalone system or may be a software component residing on the internet server. Middleware may be configured to process transactions between the various components of an application server and any number of internal or external systems for any of the purposes disclosed herein. WEBSPHERE® MQ™ (formerly MQSeries) by IBM®, Inc. (Armonk, NY) is an example of a commercially available middleware product. An Enterprise Service Bus ("ESB") application is another example of middleware.

The computers discussed herein may provide a suitable website or other internet-based graphical user interface which is accessible by users. In one embodiment, MICROSOFT® company's Internet Information Services (IIS), Transaction Server (MTS) service, and an SQL SERVER® database, are used in conjunction with MICROSOFT® operating systems, WINDOWS NT® web server software, SQL SERVER® database, and MICROSOFT® Commerce Server. Additionally, components such as ACCESS® software, SQL SERVER® database, ORACLE® software, SYBASE® software, INFORMIX® software, MYSQL® software, INTERBASE® software, etc., may be used to provide an Active Data Object (ADO) compliant database management system. In one embodiment, the APACHE® web server is used in conjunction with a LINUX® operating system, a MYSQL® database, and PERL®, PHP, Ruby, and/or PYTHON® programming languages.

For the sake of brevity, conventional data networking, application development, and other functional aspects of the systems (and components of the individual operating components of the systems) may not be described in detail herein. Furthermore, the connecting lines shown in the various FIGURES contained herein are intended to represent exemplary functional relationships and/or physical couplings between the various elements. It should be noted that many alternative or additional functional relationships or physical connections may be present in a practical system.

In various embodiments, the embodiments are directed toward one or more computer systems capable of carrying out the functionalities described herein. The computer system includes one or more processors. The processor is connected to a communication infrastructure (e.g., a communications bus, cross over bar, network, etc.). Various software embodiments are described in terms of this exemplary computer system. After reading this description, it will become apparent to a person skilled in the relevant art(s) how to implement various embodiments using other computer systems and/or architectures. The computer system can include a display interface that forwards graphics, text, and other data from the communication infrastructure (or from a frame buffer not shown) for display on a display unit.

The computer system also includes a main memory, such as random access memory (RAM), and may also include a secondary memory. The secondary memory may include, for example, a hard disk drive, a solid-state drive, and/or a removable storage drive. The removable storage drive reads from and/or writes to a removable storage unit in a well-known manner. As will be appreciated, the removable storage unit includes a computer usable storage medium having stored therein computer software and/or data.

In various embodiments, secondary memory may include other similar devices for allowing computer programs or other instructions to be loaded into a computer system. Such devices may include, for example, a removable storage unit and an interface. Examples of such may include a program cartridge and cartridge interface (such as that found in video game devices), a removable memory chip (such as an erasable programmable read only memory (EPROM), programmable read only memory (PROM)) and associated socket, or other removable storage units and interfaces, which allow software and data to be transferred from the removable storage unit to a computer system.

The terms "computer program medium," "computer usable medium," and "computer readable medium" are used to generally refer to media such as removable storage drive and a hard disk installed in hard disk drive. These computer program products provide software to a computer system.

The computer system may also include a communications interface. A communications interface allows software and data to be transferred between the computer system and external devices. Examples of such a communications interface may include a modem, a network interface (such as an Ethernet card), a communications port, etc. Software and data transferred via the communications interface are in the form of signals which may be electronic, electromagnetic, optical, or other signals capable of being received by communications interface. These signals are provided to communications interface via a communications path (e.g., channel). This channel carries signals and may be implemented using wire, cable, fiber optics, a telephone line, a cellular link, a radio frequency (RF) link, wireless and other communications channels.

As used herein an "identifier" the identifies a patient, hospital or provider may be any suitable identifier that uniquely identifies an item. For example, the identifier may be a globally unique identifier ("GUID"). The GUID may be an identifier created and/or implemented under the universally unique identifier standard. Moreover, the GUID may be stored as 128-bit value that can be displayed as 32 hexadecimal digits. The identifier may also include a major number, and a minor number. The major number and minor number may each be 16-bit integers.

In various embodiments, the system may be web based and the server may include application servers (e.g., WEBSPHERE®, WEBLOGIC®, JBOSS®, POSTGRES PLUS ADVANCED SERVER®, etc.). In various embodiments, the server may include web servers (e.g., Apache, IIS, GOOGLE® Web Server, SUN JAVA® System Web Server, JAVA® Virtual Machine running on LINUX® or WINDOWS® operating systems).

A web client includes any device or software which communicates via any network, such as, for example any device or software discussed herein. The web client may include internet browsing software installed within a computing unit or system to conduct online transactions and/or communications. These computing units or systems may take the form of a computer or set of computers, although other types of computing units or systems may be used, including personal computers, laptops, notebooks, tablets, smart phones, cellular phones, personal digital assistants, servers, pooled servers, mainframe computers, distributed computing clusters, kiosks, terminals, point of sale (POS) devices or terminals, televisions, or any other device capable of receiving data over a network. The web client may include an operating system (e.g., WINDOWS®, WINDOWS MOBILE® operating systems, UNIX® operating system, LINUX® operating systems, APPLE® OS® operating systems, etc.) as well as various conventional support software and drivers typically associated with computers. The web-client may also run MICROSOFT® INTERNET EXPLORER® software, MOZILLA® FIREFOX® software, GOOGLE CHROME™ software, APPLE® SAFARI® software, or any other of the myriad software packages available for browsing the internet.

As those skilled in the art will appreciate, the web client may or may not be in direct contact with the server (e.g., application server, web server, etc., as discussed herein). For example, the web client may access the services of the server through another server and/or hardware component, which may have a direct or indirect connection to an internet server. For example, the web client may communicate with the server via a load balancer. In various embodiments, web client access is through a network or the internet through a commercially-available web-browser software package. In that regard, the web client may be in a home or business environment with access to the network or the internet. The web client may implement security protocols such as Secure Sockets Layer (SSL) and Transport Layer Security (TLS). A web client may implement several application layer protocols including HTTP, HTTPS, FTP, and SFTP.

The various system components may be independently, separately, or collectively suitably coupled to the network via data links which includes, for example, a connection to an Internet Service Provider (ISP) over the local loop as is typically used in connection with standard modem communication, cable modem, DISH NETWORK®, ISDN, Digital Subscriber Line (DSL), or various wireless communication methods. It is noted that the network may be implemented as other types of networks, such as an interactive television (ITV) network. Moreover, the system contemplates the use, sale, or distribution of any goods, services, or information over any network having similar functionality described herein.

The system contemplates uses in association with web services, utility computing, pervasive and individualized computing, security and identity solutions, autonomic computing, cloud computing, commodity computing, mobility and wireless solutions, open source, biometrics, grid computing, and/or mesh computing.

Any of the communications, inputs, storage, databases or displays discussed herein may be facilitated through a website having web pages. The term "web page" as it is used herein is not meant to limit the type of documents and applications that might be used to interact with the user. For example, a typical website might include, in addition to standard HTML documents, various forms, JAVA® applets, JAVASCRIPT® programs, active server pages (ASP), common gateway interface scripts (CGI), extensible markup language (XML), dynamic HTML, cascading style sheets (CSS), AJAX (Asynchronous JAVASCRIPT And XML) programs, helper applications, plug-ins, and the like. A server may include a web service that receives a request from a web server, the request including a URL and an IP address (192.168.1.1). The web server retrieves the appropriate web pages and sends the data or applications for the web pages to the IP address. Web services are applications that are capable of interacting with other applications over a communications means, such as the internet. Web services are typically based on standards or protocols such as XML, SOAP, AJAX, WSDL and UDDI. Web services methods are well known in the art, and are covered in many standard texts. For example, representational state transfer (REST), or RESTful, web services may provide one way of enabling interoperability between applications.

The computing unit of the web client may be further equipped with an internet browser connected to the internet or an intranet using standard dial-up, cable, DSL, or any other internet protocol known in the art. Transactions originating at a web client may pass through a firewall in order to prevent unauthorized access from users of other networks. Further, additional firewalls may be deployed between the varying components of CMS to further enhance security.

Encryption may be performed by way of any of the techniques now available in the art or which may become available—e.g., Twofish, RSA, El Gamal, Schorr signature, DSA, PGP, PKI, GPG (GnuPG), HPE Format-Preserving Encryption (FPE), Voltage, Triple DES, Blowfish, AES, MD5, HMAC, IDEA, RC6, and symmetric and asymmetric cryptosystems. The systems and methods may also incorporate SHA series cryptographic methods, elliptic curve cryptography (e.g., ECC, ECDH, ECDSA, etc.), and/or other post-quantum cryptography algorithms under development.

The firewall may include any hardware and/or software suitably configured to protect CMS components and/or enterprise computing resources from users of other networks. Further, a firewall may be configured to limit or restrict access to various systems and components behind the firewall for web clients connecting through a web server. Firewall may reside in varying configurations including Stateful Inspection, Proxy based, access control lists, and Packet Filtering among others. Firewall may be integrated within a web server or any other CMS components or may further reside as a separate entity. A firewall may implement network address translation ("NAT") and/or network address port translation ("NAPT"). A firewall may accommodate various tunneling protocols to facilitate secure communications, such as those used in virtual private networking. A firewall may implement a demilitarized zone ("DMZ") to facilitate communications with a public network such as the internet. A firewall may be integrated as software within an internet server or any other application server components, reside within another computing device, or take the form of a standalone hardware component.

Any databases discussed herein may include relational, hierarchical, graphical, blockchain, object-oriented structure, and/or any other database configurations. Any database may also include a flat file structure wherein data may be stored in a single file in the form of rows and columns, with no structure for indexing and no structural relationships between records. For example, a flat file structure may include a delimited text file, a CSV (comma-separated values) file, and/or any other suitable flat file structure. Common database products that may be used to implement the databases include DB2® by IBM® (Armonk, NY), various database products available from ORACLE® Corporation (Redwood Shores, CA), MICROSOFT ACCESS® or MICROSOFT SQL SERVER® by MICROSOFT® Corporation (Redmond, WA), MYSQL® by MySQL AB (Uppsala, Sweden), MONGODB®, Redis, APACHE CASSANDRA®, HBASE® by APACHE®, MapR-DB by the MAPR® corporation, or any other suitable database product. Moreover, any database may be organized in any suitable manner, for example, as data tables or lookup tables.

Each record may be a single file, a series of files, a linked series of data fields, or any other data structure.

As used herein, big data may refer to partially or fully structured, semi-structured, or unstructured data sets including millions of rows and hundreds of thousands of columns. A big data set may be compiled, for example, from a history of purchase transactions over time, from web registrations, from social media, from records of charge (ROC), from summaries of charges (SOC), from internal data, or from other suitable sources. Big data sets may be compiled without descriptive metadata such as column types, counts, percentiles, or other interpretive-aid data points.

Association of certain data may be accomplished through any desired data association technique such as those known or practiced in the art. For example, the association may be accomplished either manually or automatically. Automatic association techniques may include, for example, a database search, a database merge, GREP, AGREP, SQL, using a key field in the tables to speed searches, sequential searches through all the tables and files, sorting records in the file according to a known order to simplify lookup, and/or the like. The association step may be accomplished by a database merge function, for example, using a "key field" in pre-selected databases or data sectors. Various database tuning steps are contemplated to optimize database performance. For example, frequently used files such as indexes may be placed on separate file systems to reduce In/Out ("I/O") bottlenecks.

More particularly, a "key field" partitions the database according to the high-level class of objects defined by the key field. For example, certain types of data may be designated as a key field in a plurality of related data tables and the data tables may then be linked on the basis of the type of data in the key field. The data corresponding to the key field in each of the linked data tables is preferably the same or of the same type. However, data tables having similar, though not identical, data in the key fields may also be linked by using AGREP, for example. In accordance with one embodiment, any suitable data storage technique may be utilized to store data without a standard format. Data sets may be stored using any suitable technique, including, for example, storing individual files using an ISO/IEC 7816-4 file structure; implementing a domain whereby a dedicated file is selected that exposes one or more elementary files containing one or more data sets; using data sets stored in individual files using a hierarchical filing system; data sets stored as records in a single file (including compression, SQL accessible, hashed via one or more keys, numeric, alphabetical by first tuple, etc.); data stored as Binary Large Object (BLOB); data stored as ungrouped data elements encoded using ISO/IEC 7816-6 data elements; data stored as ungrouped data elements encoded using ISO/IEC Abstract Syntax Notation (ASN.1) as in ISO/IEC 8824 and 8825; other proprietary techniques that may include fractal compression methods, image compression methods, etc.

In various embodiments, the ability to store a wide variety of information in different formats is facilitated by storing the information as a BLOB. Thus, any binary information can be stored in a storage space associated with a data set. As discussed above, the binary information may be stored in association with the system or external to but affiliated with the system. The BLOB method may store data sets as ungrouped data elements formatted as a block of binary via a fixed memory offset using either fixed storage allocation, circular queue techniques, or best practices with respect to memory management (e.g., paged memory, least recently used, etc.). By using BLOB methods, the ability to store various data sets that have different formats facilitates the storage of data, in the database or associated with the system, by multiple and unrelated owners of the data sets. For example, a first data set which may be stored may be provided by a first party, a second data set which may be stored may be provided by an unrelated second party, and yet a third data set which may be stored may be provided by a third party unrelated to the first and second party. Each of these three exemplary data sets may contain different information that is stored using different data storage formats and/or techniques. Further, each data set may contain subsets of data that also may be distinct from other subsets.

As stated above, in various embodiments, the data can be stored without regard to a common format. However, the data set (e.g., BLOB) may be annotated in a standard manner when provided for manipulating the data in the database or system. The annotation may comprise a short header, trailer, or other appropriate indicator related to each data set that is configured to convey information useful in managing the various data sets. For example, the annotation may be called a "condition header," "header," "trailer," or "status," herein, and may comprise an indication of the status of the data set or may include an identifier correlated to a specific issuer or owner of the data. In one example, the first three bytes of each data set BLOB may be configured or configurable to indicate the status of that particular data set; e.g., LOADED, INITIALIZED, READY, BLOCKED, REMOVABLE, or DELETED. Subsequent bytes of data may be used to indicate for example, the identity of the issuer, user, transaction/membership account identifier or the like. Each of these condition annotations are further discussed herein.

The data set annotation may also be used for other types of status information as well as various other purposes. For example, the data set annotation may include security information establishing access levels. The access levels may, for example, be configured to permit only certain individuals, levels of employees, companies, or other entities to access data sets, or to permit access to specific data sets based on the transaction, merchant, issuer, user, or the like. Furthermore, the security information may restrict/permit only certain actions, such as accessing, modifying, and/or deleting data sets. In one example, the data set annotation indicates that only the data set owner or the user are permitted to delete a data set, various identified users may be permitted to access the data set for reading, and others are altogether excluded from accessing the data set. However, other access restriction parameters may also be used allowing various entities to access a data set with various permission levels as appropriate.

The data, including the header or trailer, may be received by a standalone interaction device configured to add, delete, modify, or augment the data in accordance with the header or trailer. As such, in one embodiment, the header or trailer is not stored on the transaction device along with the associated issuer-owned data, but instead the appropriate action may be taken by providing to the user, at the standalone device, the appropriate option for the action to be taken. The system may contemplate a data storage arrangement wherein the header or trailer, or header or trailer history, of the data is stored on the system, device or transaction instrument in relation to the appropriate data.

One skilled in the art will also appreciate that, for security reasons, any databases, systems, devices, servers, or other components of the system may consist of any combination thereof at a single location or at multiple locations, wherein each database or system includes any of various suitable security features, such as firewalls, access codes, encryption, decryption, compression, decompression, and/or the like.

Practitioners will also appreciate that there are a number of methods for displaying data within a browser-based document. Data may be represented as standard text or within a fixed list, scrollable list, drop-down list, editable text field, fixed text field, pop-up window, and the like. Likewise, there are a number of methods available for modifying data in a web page such as, for example, free text entry using a keyboard, selection of menu items, check boxes, option boxes, and the like.

The data may be big data that is processed by a distributed computing cluster. The distributed computing cluster may be, for example, a HADOOP® software cluster configured to process and store big data sets with some of nodes comprising a distributed storage system and some of nodes comprising a distributed processing system. In that regard, distributed computing cluster may be configured to support a HADOOP® software distributed file system (HDFS) as specified by the Apache Software Foundation at www.hadoop.apache.org/docs.

As used herein, the term "network" includes any cloud, cloud computing system, or electronic communications system or method which incorporates hardware and/or software components. Communication among the parties may be accomplished through any suitable communication channels, such as, for example, a telephone network, an extranet, an intranet, internet, point of interaction device (point of sale device, personal digital assistant (e.g., an IPHONE® device, a BLACKBERRY® device), cellular phone, kiosk, etc.), online communications, satellite communications, off-line communications, wireless communications, transponder communications, local area network (LAN), wide area network (WAN), virtual private network (VPN), networked or linked devices, keyboard, mouse, and/or any suitable communication or data input modality. Moreover, although the system is frequently described herein as being implemented with TCP/IP communications protocols, the system may also be implemented using IPX, APPLETALK® program, IP-6, NetBIOS, OSI, any tunneling protocol (e.g. IPsec, SSH, etc.), or any number of existing or future protocols. If the network is in the nature of a public network, such as the internet, it may be advantageous to presume the network to be insecure and open to eavesdroppers. Specific information related to the protocols, standards, and application software utilized in connection with the internet is generally known to those skilled in the art and, as such, need not be detailed herein.

"Cloud" or "Cloud computing" includes a model for enabling convenient, on-demand network access to a shared pool of configurable computing resources (e.g., networks, servers, storage, applications, and services) that can be rapidly provisioned and released with minimal management effort or service provider interaction. Cloud computing may include location-independent computing, whereby shared servers provide resources, software, and data to computers and other devices on demand.

As used herein, "transmit" may include sending electronic data from one system component to another over a network connection. Additionally, as used herein, "data" may include encompassing information such as commands, queries, files, data for storage, and the like in digital or any other form.

Any database discussed herein may comprise a distributed ledger maintained by a plurality of computing devices (e.g., nodes) over a peer-to-peer network. Each computing device maintains a copy and/or partial copy of the distributed ledger and communicates with one or more other computing devices in the network to validate and write data to the distributed ledger. The distributed ledger may use features and functionality of blockchain technology, including, for example, consensus-based validation, immutability, and cryptographically chained blocks of data. The blockchain may comprise a ledger of interconnected blocks containing data. The blockchain may provide enhanced security because each block may hold individual transactions and the results of any blockchain executables. Each block may link to the previous block and may include a timestamp. Blocks may be linked because each block may include the hash of the prior block in the blockchain. The linked blocks form a chain, with only one successor block allowed to link to one other predecessor block for a single chain. Forks may be possible where divergent chains are established from a previously uniform blockchain, though typically only one of the divergent chains will be maintained as the consensus chain. In various embodiments, the blockchain may implement smart contracts that enforce data workflows in a decentralized manner. The system may also include applications deployed on user devices such as, for example, computers, tablets, smartphones, Internet of Things devices ("IoT" devices), etc. The applications may communicate with the blockchain (e.g., directly or via a blockchain node) to transmit and retrieve data. In various embodiments, a governing organization or consortium may control access to data stored on the blockchain. Registration with the managing organization(s) may enable participation in the blockchain network.

Data transfers performed through the blockchain-based system may propagate to the connected peers within the blockchain network within a duration that may be determined by the block creation time of the specific blockchain technology implemented. For example, on an ETHEREUM®-based network, a new data entry may become available within about 13-20 seconds as of the writing. On a HYPERLEDGER® Fabric 1.0 based platform, the duration is driven by the specific consensus algorithm that is chosen, and may be performed within seconds. In that respect, propagation times in the system may be improved compared to existing systems, and implementation costs and time to market may also be drastically reduced. The system also offers increased security at least partially due to the immutable nature of data that is stored in the blockchain, reducing the probability of tampering with various data inputs and outputs. Moreover, the system may also offer increased security of data by performing cryptographic processes on the data prior to storing the data on the blockchain. Therefore, by transmitting, storing, and accessing data using the system described herein, the security of the data is improved, which decreases the risk of the computer or network from being compromised.

In various embodiments, the system may also reduce database synchronization errors by providing a common data structure, thus at least partially improving the integrity of stored data. The system also offers increased reliability and fault tolerance over traditional databases (e.g., relational databases, distributed databases, etc.) as each node operates with a full copy of the stored data, thus at least partially reducing downtime due to localized network outages and hardware failures. The system may also increase the reliability of data transfers in a network environment having reliable and unreliable peers, as each node broadcasts messages to all connected peers, and, as each block comprises a link to a previous block, a node may quickly detect a missing block and propagate a request for the missing block to the other nodes in the blockchain network.

The particular blockchain implementation described herein provides improvements over conventional technology by using a decentralized database and improved processing environments. In particular, the blockchain implementation improves computer performance by, for example, leveraging decentralized resources (e.g., lower latency). The distributed computational resources improves computer performance by, for example, reducing processing times. Furthermore, the distributed computational resources improves computer performance by improving security using, for example, cryptographic protocols.

The system may obtain information or content about the patient from any source or channel. Any communication, transmission, and/or channel discussed herein may include any system or method for delivering content (e.g. data, information, metadata, etc.), and/or the content itself. The content may be presented in any form or medium, and in various embodiments, the content may be delivered electronically and/or capable of being presented electronically. For example, a channel may comprise a website, mobile application, or device (e.g., FACEBOOK®, YOUTUBE®, PANDORA®, APPLE TV®, MICROSOFT® XBOX®, ROKU®, AMAZON FIRE®, GOOGLE CHROMECAST™, SONY® PLAYSTATION®, NINTENDO® SWITCH®, etc.) a uniform resource locator ("URL"), a document (e.g., a MICROSOFT® Word or EXCEL™, an ADOBE® Portable Document Format (PDF) document, etc.), an "ebook," an "emagazine," an application or microapplication (as described herein), an short message service (SMS) or other type of text message, an email, a FACEBOOK® message, a TWITTER® tweet, multimedia messaging services (MMS), and/or other type of communication technology. In various embodiments, a channel may be hosted or provided by a data partner. In various embodiments, the distribution channel may comprise at least one of a merchant website, a social media website, affiliate or partner websites, an external vendor, a mobile device communication, social media network, and/or location based service. Distribution channels may include at least one of a merchant website, a social media site, affiliate or partner websites, an external vendor, and a mobile device communication. Examples of social media sites include FACEBOOK®, FOURSQUARE®, TWITTER®, LINKEDIN®, INSTAGRAM®, PINTEREST®, TUMBLR®, REDDIT®, SNAPCHAT®, WHATSAPP®, FLICKR®, VK®, QZONE®, WECHAT®, and the like. Examples of affiliate or partner websites include AMERICAN EXPRESS®, GROUPON®, LIVINGSOCIAL®, and the like. Moreover, examples of mobile device communications include texting, email, and mobile applications for smartphones.

What is claimed is:

1. A method comprising:
receiving, by a computer, variables of patient health data for each patient within a panel of patients for one or more medical providers, wherein the variables comprise lab values and vital signs;
determining, by the computer, a likelihood of an adverse health outcome based on at least one of a likelihood of hospitalization of each patient within the panel of patients within a time period, a likelihood of a fall sustained by each patient within the panel of patients within the time period or a likelihood of a death of each patient within the panel of patients in the time period;
determining, by the computer using the multi-attribute value function, a first rank order correlation of the lab values common to a subset of the patients within the panel of patients for the one or more medical providers, with the likelihood of the adverse health outcome for each patient within the panel of patients for the one or more medical providers, wherein the first rank order correlation determines a statistical dependence between a ranking of the lab values and the likelihood of the adverse health outcome for the panel of patients;
determining, by the computer using the multi-attribute value function, a second rank order correlation of the vital signs common to the subset of the patients within the panel of patients for the one or more medical providers, with the likelihood of the adverse health outcome for each patient within the panel of patients for the one or more medical providers, wherein the second rank order correlation determines a statistical dependence between a ranking of the vital signs and the likelihood of the adverse health outcome for the panel of patients;
determining, by the computer using the multi-attribute value function, a risk score for the patient based on the first rank order correlation, the second rank order correlation and a weighting of the panel of patients;
sorting, by the computer, the panel of patients based on the risk score for each patient in the panel of patients;
lowering, by the computer, a timeframe to a lowered timeframe on a timer for allocating healthcare resources for the patient, in response to the risk score for the patient being higher than other risk scores for other patients in the panel of patients; and
setting, by the computer, the timer for the lowered timeframe, in response to the allocating the healthcare resources.

2. The method of claim 1, further comprising:
adding, by the computer, the risk score for each of the patients in the panel of patients that are handled by one or more of the medical providers to create a medical provider patient panel risk score; and
determining, by the computer, a reimbursement to the one or more medical providers based on the medical provider patient panel risk score and quality of care provided by the healthcare resource.

3. The method of claim 1, further comprising:
receiving, by the computer, a signal from a chart indicating that at least one of the chart was accessed by the one or more medical providers or a note was written in the chart; and
resetting, by the computer, the timer in response to the receiving the signal from the chart.

4. The method of claim 1, wherein the risk score is based on the weighting of each patient of the panel of patients and (the lab values*the lab values correlation with the adverse health outcome)+(the vital signs*the vital signs correlation with the adverse health outcome).

5. The method of claim 1, further comprising associating, by the computer, the timer with a chart for each patient in the panel of patients.

6. The method of claim 1, further comprising sending, by the computer, a notification to at least one of an app or device associated with the patient.

7. The method of claim 1, further comprising sending, by the computer, at least one of a notification to a shopping list to suggest buying new or different types of food, a notification to a health app to increase or decrease certain exercises, a notification to the health app to schedule testing or to schedule a physician appointment, or a notification to the health app to restrict workouts that cause the patient to increase heart rate or blood oxygen above a certain level.

8. The method of claim 1, further comprising queuing, by the computer, a chart higher in a queue, in response to the risk score for the patient being higher than other risk scores for other patients in the panel of patients.

9. The method of claim 1, further comprising notifying, by the computer, the one or more medical providers, in response to the timer being at a predetermined time.

10. A system comprising:
one or more processors; and
one or more tangible, non-transitory memories configured to communicate with the one or more processors,
the one or more tangible, non-transitory memories having instructions stored thereon that, in response to execution by the one or more processors, cause the one or more processors to perform operations comprising:
receiving, by the one or more processors, variables of patient health data for each patient within a panel of patients for one or more medical providers, wherein the variables comprise lab values and vital signs;
determining, by the one or more processors, a likelihood of an adverse health outcome based on at least one of a likelihood of hospitalization of each patient within the panel of patients within a time period, a likelihood of a fall sustained by each patient within the panel of patients within the time period or a likelihood of a death of each patient within the panel of patients in the time period;
determining, by the one or more processors using the multi-attribute value function, a first rank order correlation of the lab values common to a subset of the patients within the panel of patients for the one or more medical providers, with the likelihood of the adverse health outcome for each patient within the panel of patients for the one or more medical providers, wherein the first rank order correlation determines a statistical dependence between a ranking of the lab values and the likelihood of the adverse health outcome for the panel of patients;
determining, by the one or more processors using the multi-attribute value function, a second rank order correlation of the vital signs common to the subset of the patients within the panel of patients for the one or more medical providers, with the likelihood of the adverse health outcome for each patient within the panel of patients for the one or more medical providers, wherein the second rank order correlation determines a statistical dependence between a ranking of the vital signs and the likelihood of the adverse health outcome for the panel of patients;
determining, by the one or more processors using the multi-attribute value function, a risk score for the patient based on the first rank order correlation, the second rank order correlation and a weighting of the panel of patients;
sorting, by the one or more processors, the panel of patients based on the risk score for each patient in the panel of patients;
lowering, by the one or more processors, a timeframe to a lowered timeframe on a timer for allocating healthcare resources for the patient, in response to the risk score for the patient being higher than other risk scores for other patients in the panel of patients; and setting, by the one or more processors, the timer for the lowered timeframe, in response to the allocating the healthcare resources.

11. The method of claim 1, further comprising periodically updating, by the computer, at least one of the first rank order correlation or the second rank order correlation.

12. The method of claim 1, further comprising re-arranging, by the computer, names of patients to include the names of patients with higher risk scores at the top of a list on a display.

13. The method of claim 1, wherein the first rank order correlation is high when observations have a similar rank between the lab values and the likelihood of the adverse health outcome, and the first rank order correlation between the lab values and the likelihood of the adverse health outcome is low when observations have a dissimilar rank between the lab values and the likelihood of the adverse health outcome.

14. The method of claim 1, wherein the determining at least one of the first rank order correlation or the second rank order correlation is based on a time period.

15. The method of claim 1, further comprising:
determining, by the computer using the multi-attribute value function, a third rank order correlation of at least one of age or weight common to the subset of the patients within the panel of patients for the one or more medical providers, with the likelihood of the adverse health outcome for each patient within the panel of patients for the one or more medical providers, wherein the third rank order correlation determines a statistical dependence between a ranking of the at least one of age or weight and the likelihood of the adverse health outcome; and
determining, by the computer using the multi-attribute value function, a risk score for the patient based on the first rank order correlation, the second rank order correlation and the third rank order correlation.

16. The method of claim 1, further comprising notifying, by the computer, one or more of the medical providers that the timer exceeded the lowered timeframe, wherein the notifying comprises at least one of sending a text, flashing a computer screen, displaying a chart of the patient or notifying an assistant of one or more of the medical providers.

17. The method of claim 1, further comprising re-setting, by the computer, the timer based on receiving a signal about an action by one or more of the medical providers.

18. The method of claim 17, wherein the action includes at least one of opening a medical chart, viewing the lab value, writing a note in the medical chart, documenting a finding in the medical chart or documenting an encounter with the patient.

19. The method of claim 1, further comprising displaying, by the computer, on a screen each patient in the panel of patients in an order of the risk score.

20. The method of claim 1, further comprising setting, by the computer and in response to an action, an appointment for the patient with one or more of the medical providers by integrating with a scheduling system and a calendar of the patient.

* * * * *